US012629539B2

(12) United States Patent
Carstensen et al.

(10) Patent No.: US 12,629,539 B2
(45) Date of Patent: May 19, 2026

(54) MODULATION OF THE THETA-GAMMA NEURAL CODE WITH CONTROLLED LIGHT THERAPEUTICS

(71) Applicant: Optoceutics ApS, Kongens Lyngby (DK)

(72) Inventors: Marcus Carstensen, Frederiksberg C (DK); Ngoc Mai Nguyen, San Jose, CA (US)

(73) Assignee: OptoCeutics ApS, Berkeley, CA (US)

( * ) Notice: Subject to any disclaimer, the term of this patent is extended or adjusted under 35 U.S.C. 154(b) by 1007 days.

(21) Appl. No.: 17/507,275

(22) Filed: Oct. 21, 2021

(65) Prior Publication Data

US 2023/0126680 A1 Apr. 27, 2023

(51) Int. Cl.
A61N 5/06 (2006.01)
A61B 5/00 (2006.01)
(Continued)

(52) U.S. Cl.
CPC .......... A61N 5/0622 (2013.01); A61B 5/0077 (2013.01); A61B 5/163 (2017.08);
(Continued)

(58) Field of Classification Search
None
See application file for complete search history.

(56) References Cited

U.S. PATENT DOCUMENTS 8,597,171 B2 12/2013 Altman
10,279,192 B2 5/2019 Malchano et al.
(Continued)

FOREIGN PATENT DOCUMENTS

EP 4210812 A1 7/2023
JP 2021/194356 A 12/2021
(Continued)

OTHER PUBLICATIONS

Gamma oscillations in the entorhinal-hippocampal circuit underlying memory and dementia. Tomoaki Nakazono. Neurosci Res. Apr. 2018 ; 129: 40-46.
(Continued)

*Primary Examiner* — Jason M Sims
*Assistant Examiner* — Matthew Eric Ogles
(74) *Attorney, Agent, or Firm* — Patent Law Group; Brian Ogonowsky

(57) ABSTRACT

Gamma brain stimulation (around 40 Hz) is performed using light pulses. To perform theta brain stimulation (around 7 Hz) without perceptible flicker, the light source is also strobed at 47 Hz (also within the gamma range). The brain perceives the 40 Hz and a subtraction frequency of 7 Hz (in the theta range). The combined gamma and theta wave stimulation of the brain may be used for preventing or treating brain disease or sleeping disorders. The particular stimulation frequencies and their phases create neuronal gamma-theta coupling in the brain that has been shown to have positive effects on memory, Alzheimer's disease, motor skills, and other functions. Other gamma and theta frequencies, creating gamma-theta coupling in the brain, are also beneficial. The phase of the light pulses is also dynamically controlled using feedback to maximize theta-gamma coupling in the brain.

18 Claims, 5 Drawing Sheets

(51) Int. Cl.

| | |
|---|---|
| *A61B 5/16* | (2006.01) |
| *A61B 5/374* | (2021.01) |
| *A61B 5/375* | (2021.01) |
| *A61B 5/378* | (2021.01) |

(52) U.S. Cl.
CPC .............. *A61B 5/374* (2021.01); *A61B 5/375* (2021.01); *A61B 5/378* (2021.01); *A61B 5/4836* (2013.01); *A61N 2005/0626* (2013.01); *A61N 2005/0651* (2013.01)

(56) References Cited

U.S. PATENT DOCUMENTS

| | | | | |
|---|---|---|---|---|
| 10,328,276 | B2 | 6/2019 | Williams et al. | |
| 11,235,169 | B1 * | 2/2022 | Osterloh | A61N 5/0616 |
| 2014/0058483 | A1 * | 2/2014 | Zao | A61N 5/06 |
| | | | | 607/88 |
| 2019/0126062 | A1 * | 5/2019 | Adaikkan | A61N 5/0622 |
| 2019/0255350 | A1 * | 8/2019 | Malchano | A61N 1/36132 |
| 2020/0360715 | A1 | 11/2020 | Lim | |
| 2021/0290970 | A1 * | 9/2021 | Hunter | A61N 1/403 |
| 2022/0406271 | A1 * | 12/2022 | Chen | |
| 2023/0270368 | A1 * | 8/2023 | Kim | A61H 5/00 |
| | | | | 600/559 |

FOREIGN PATENT DOCUMENTS

| | | |
|---|---|---|
| WO | WO 2022/056002 | 3/2022 |
| WO | WO 2022/056002 A1 | 3/2022 |

OTHER PUBLICATIONS

Safety, Feasibility, and Potential Clinical Efficacy of 40Hz Invisible Spectral Flicker versus Placebo . . . . Mikkel Agger. Journal of Alzheimer's Disease (2023).

PCT search report, Feb. 27, 2023.

SSVEP At Single and Beating Frequencies Utilizing Perceptual Insights, Sant, et al. Thesis, Radbound University, Nijmegen. Jun. 29, 2012.

Belluscio et al., Cross-Frequency Phase-Phase Coupling Between Theta and Gamma Oscillations in the Hippocampus, Journal of Neuroscience, Jan. 11, 2012.

PCT ISR mailed Jun. 26, 2024.

Extended European Search Report, Application 22884528.5, PCT/US2022047432.

* cited by examiner

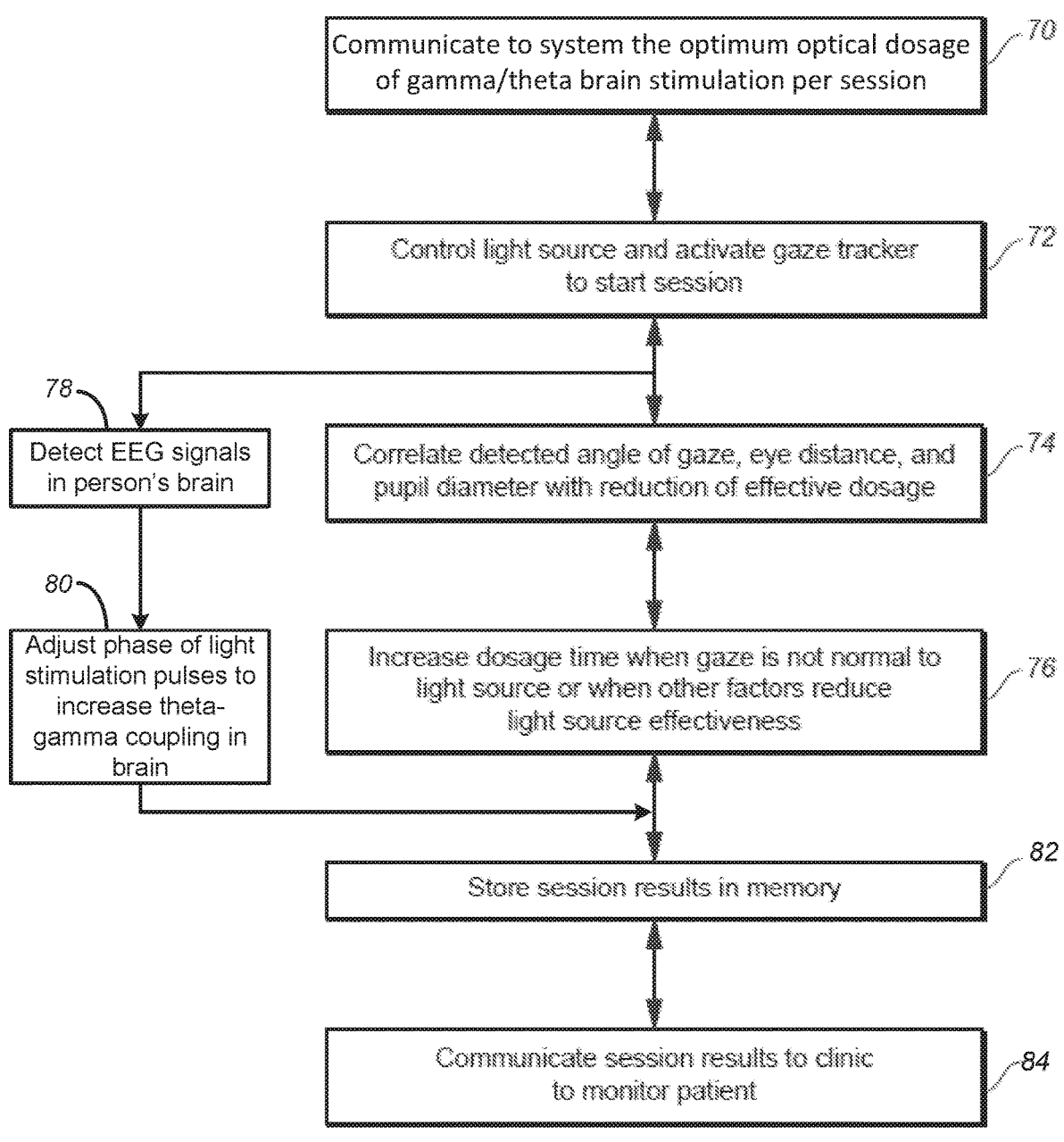

Communicate to system the optimum optical dosage of gamma/theta brain stimulation per session — 70

Control light source and activate gaze tracker to start session — 72

78 — Detect EEG signals in person's brain

Correlate detected angle of gaze, eye distance, and pupil diameter with reduction of effective dosage — 74

80 — Adjust phase of light stimulation pulses to increase theta-gamma coupling in brain Increase dosage time when gaze is not normal to light source or when other factors reduce light source effectiveness — 76

Store session results in memory — 82

Communicate session results to clinic to monitor patient — 84

FIG. 5

MODULATION OF THE THETA-GAMMA NEURAL CODE WITH CONTROLLED LIGHT THERAPEUTICS

FIELD OF THE INVENTION

The invention relates to optical (or photonic) gamma brain stimulation and theta brain stimulation for treating or preventing certain diseases, such as Alzheimer's disease, dementia, circadian rhythm sleep disorders, and other brain disorders.

BACKGROUND

Research has provided evidence in mice that stimulation of gamma brain waves reduces Alzheimer's-related proteins and slows neurodegeneration associated with the disease. Gamma brain waves are electrical charges that help link and process information from all parts of the brain. It is believed that similar advantageous effects occur in humans, and such research is on-going.

Healthy brains feature rhythmic patterns, or brain waves, that operate at different frequencies. Gamma brain waves, which oscillate at roughly from 20 to 140 Hz, are associated with higher-order cognitive functions and are known to decrease in the brains of people with Alzheimer's disease and other neurological or psychiatric disorders.

It has been discovered that exposing Alzheimer's mouse models to visible-wavelength LED lights flickering (i.e., strobing) at 40 Hz stimulates gamma waves, which not only reduces levels of beta-amyloid and tau (proteins associated with Alzheimer's) but also boosts the activity of microglia in clearing harmful debris. In other words, such strobing triggers brain wave oscillations around 40 Hz.

Further details of the effects of optical gamma brain stimulation can be found in published applications WO2018/152255 and US 2020/0269065, both incorporated herein by reference. Many more publications describe such effects.

Gamma wave stimulation using sound (e.g., clicks played at 40 Hz) in Alzheimer's mouse models has related positive effects.

Using optical or sound gamma stimulation resulted in stimulated mice performing better on memory tasks, including recognizing objects and navigating a water maze to find a hidden platform. Researchers also saw changes in activation responses in microglia and astrocytes (cells involved in clearing debris) and in blood vessels.

Mice exposed to a combination of light and sound gamma stimulation expanded the effects beyond the visual and auditory cortex to the prefrontal cortex, an area of the brain important for planning and completing tasks. Using imaging analysis, the scientists found a unique clustering effect of microglia around amyloid deposits in stimulated mice and reduced amyloid pathology. The effects were short-lived, however, diminishing a week after stimulation.

In a study published in the periodical Neuron, MIT researchers tested the effects of longer-term treatment by exposing mouse models with more advanced Alzheimer's disease to up to six weeks of gamma entrainment by visual stimulation. Results showed stimulation increased gamma brain waves in the visual cortex and higher-order brain areas, including the hippocampus and prefrontal cortex. Continuing stimulation also preserved neuronal and synaptic density in these brain regions, improved performance on memory tasks, and reduced inflammation. Findings point to an overall neuroprotective effect, even in the later stages of neurodegeneration, the researchers reported.

Results of this research add to previous investigations of gamma wave stimulation as a possible treatment for Alzheimer's disease in humans.

40 Hz light stimulation has been shown to not only synchronize with the visual cortex, but also synchronize with the hippocampus and the frontal cortex (measured and validated via implants in humans).

Using a strip of LED lights that flickered at different speeds, the researchers found that a single, hour-long treatment of light flashing at 40 Hz increased gamma waves and reduced beta-amyloid levels by half in the visual cortex of mice in the very early stages of Alzheimer's. Within 24 hours, however, amyloid levels returned to normal in this brain region, which processes information from the eyes. When the scientists exposed mice with even higher levels of amyloid buildup to one hour of flickering light per day over seven days, the number of amyloid plaques and levels of free-floating amyloid decreased. The treatment also ramped up the efficiency of microglia, reducing the number of amyloid plaques and free-floating amyloid.

As seen, repeated treatments are required for the gamma brain stimulation, and optimal dosages of the gamma brain stimulation light are being determined.

The brain also produces theta waves in the 4-10 Hz range. Theta waves generate the theta rhythm, a neural oscillation in the brain that underlies various aspects of cognition and behavior, including learning, memory, and spatial navigation in many animals. It can be recorded using various electrophysiological methods, such as electroencephalogram (EEG), recorded either from inside the brain or from electrodes attached to the scalp.

At least two types of theta rhythm have been described. The hippocampal theta rhythm is a strong oscillation that can be observed in the hippocampus and other brain structures in numerous species of mammals including rodents, rabbits, dogs, cats, bats, and marsupials. Cortical theta rhythms are low-frequency components of scalp EEG, usually recorded from humans. Theta rhythms can be quantified using quantitative electroencephalography (qEEG) using freely available toolboxes, such as, EEGLAB or the Neurophysiological Biomarker Toolbox (NBT).

In humans, hippocampal theta rhythm has been observed and linked to memory formation and navigation. In addition to the theta rhythm being important for hippocampal function, it is also important for long-range communication between brain regions.

As with rats, humans exhibit hippocampal theta wave activity during REM sleep. Humans also exhibit predominantly cortical theta wave activity during REM sleep. Increased sleepiness is associated with decreased alpha wave power and increased theta wave power. Meditation has been shown to increase theta power.

In a recent article in "Neuron", Ole Jensen and John Lisman explain that gamma oscillations (40 Hz) and slower theta oscillations (7 Hz) occur in the same brain regions and interact with each other, a process known as cross-frequency coupling. Jensen and Lisman propose that this cross-frequency coupling allows the brain to represent (or code) multiple pieces of information in an ordered way, and cross-frequency coupling can be used to measure the relationship between the phase of the theta oscillations and the envelope of the gamma power. Thus, high values of coupling indicate that gamma amplitude is a strong function of theta phase. See ncbi.nlm.nih.gov/pmc/articles/PMC3648857/.

Recent work suggests that this coding scheme coordinates communication between brain regions and is involved in sensory as well as memory processes.

As seen, it is believed that there are significant benefits to human mental and physical health if theta waves and gamma waves, produced in the brain, are sufficiently strong and occur at an optimal phase.

To the Applicant's knowledge, there is no user-operated system that stimulates the user's brain with combined gamma and theta waves.

One problem with optically stimulating the brain with gamma and theta waves is that the light flicker at the theta frequency of 4-10 Hz would be extremely uncomfortable to the user over an extended time and may lead to other neurological issues. However, the flicker of the gamma light frequency of 40 Hz is barely perceptible to humans.

What is needed is a non-invasive system that stimulates the brain to produce gamma and theta waves in an optimal phase and dosage to aid in preventing or slowing Alzheimer's disease or other brain diseases and/or improving memory and other skills. What is also needed is a technique for performing such stimulation without noticeable flicker of light.

SUMMARY

One object is to provide a method to stimulate the neuronal theta-gamma coupling (inside the brain) using flickering light for therapeutic and diagnostic purposes, such as treatment of Alzheimer's disease or treatment of other neurological and psychiatric disorders (i.e. brain network dysfunctions). Theta-gamma coupling (TGC) is a form of cross-frequency coupling inside the brain, whereby "high-frequency" gamma (e.g., 30-50 Hz) oscillations are modulated by low-frequency theta (e.g., 4-10 Hz) oscillations.

Using light is not required, and other sense stimulations, such as skin vibrations, electric stimulation of the skin, or sound stimulation at the gamma/theta frequencies will also produce positive benefits.

In one embodiment, a user-operated optical (or photonic) gamma and theta brain stimulation system is disclosed that flickers one or more light sources, such as white light or blue light LEDs, at a particular gamma frequency, such as at a rate of 40 Hz, and also flickers one or more white light or blue light LEDs at a rate of 47 Hz., which creates a beat frequency (or subtraction frequency) of 7 Hz (a theta frequency) inside the brain as well as a gamma frequency of 40 Hz. Alternatively, the 40 Hz stimulation may be followed within 6 seconds of the 47 Hz stimulation to have a similar effect of inducing gamma waves and theta waves in the user's brain. Thus, induced theta-gamma coupling is created in the brain with little to no experience of perceptible flicker.

Since there is no light flickering at the theta frequency, any flickering is substantially imperceptible and not annoying. Flickering is substantially imperceptible at frequencies above 30 Hz.

In another embodiment, instead of the light alternating between white and darkness, the light can alternate between two different colors at the stimulation frequencies. For example, one light source can alternate at 47 Hz between color XX and the color YY, and the other light source can alternate at 40 Hz between color ZZ and KK. This is referred to as heterochromatic flicker. The heterochromatic flicker can be constructed by multiple combinations of waveforms. Such heterochromatic flicker reduces any noticeable flicker yet produces good results. If the two colors are of equal luminance (but still different hues), the flicker should be imperceptible.

Utilizing the non-linearity, especially two-wave, three-wave, or four-wave mixing properties of the brain, other combinations of frequencies can also be generated to stimulate specific dual combinations of frequencies for multiple frequency stimulation of the Theta-Gamma coupling.

In another embodiment, the light variation is sinusoidal, and the current to the LEDs is at 40 Hz and 47 Hz. This results in stimulation of the brain at both the gamma frequency (40 Hz) and theta frequency (7 Hz).

A gamma brain stimulation rate range between 20 Hz-140 Hz may be effective, and a theta brain stimulation rate range between 4 Hz-10 Hz may be effective. Therefore, the two light flickering frequencies would differ by 4-10 Hz and be in the range of 20-150 Hz.

For a pulsed system, a duty cycle of 50% is sufficient, but the duty cycle is not critical.

Theta-gamma coupling supports memory processes in the entorhinal-hippocampal network. Lower frequency gamma modulated by theta gamma may promote memory retrieval, while higher frequency gamma modulated by theta may facilitate memory encoding.

The light source output power should be at a comfortable level for the person, such as a patient or any other person looking at it, and a precise output power does not seem critical. The optimal dosage is preprogrammed into the system. An optimal dosage for the particular person, such as a patient, may be, for example, one continuous hour every day for example at 9 am. By precisely monitoring dosages for many similar persons and storing the information, while also testing the persons for changes in the disease, a correlation can then be developed between dosage and patient improvement.

Various areas of the brain can be stimulated by optical brain stimulation treatment such as the hippocampus, amygdala, prefrontal cortex (PFC), visual cortex (VC), and the suprachiasmatic nucleus (SCN). The ability to determine the optimal target effective dosage of optical brain stimulation for these particular areas of the brain will aid in the treatment of diseases that are associated with neurodegeneration. In particular, understanding the minimal dosage required to activate the hippocampus and SCN to affect circadian rhythm (often associated with early onset of Alzheimer's) may allow for individualize/personalize treatment of diseases.

One can examine dose dependence of activation of cytokines within 15 minutes of light exposure, while it takes 60 minutes to activate autoimmune cells. So, knowing when certain enzyme and transcription/translation activation occurs is important in determining the required treatment duration (or dosage), and the treatment can be personalized to each person.

To provide a more accurate determination of the effective dosage, an eye tracking system detects the person's gaze angle relative to the light source during the stimulation session. A maximum dosage is delivered when the person is directly looking at the light source at a particular distance (e.g., 50 cm). In that case, the dosage time can be the minimum. If the person looks away from the light source for periods of time during the treatment, the non-zero gaze angle is processed using an algorithm to extend the dosage time so the person receives the overall correct dosage for the day.

The gaze tracker can also determine the distance the eye is from the light source and the diameter of the pupil. These factors also affect the effective dosage, and the system dynamically controls the dosage time or even the light output power to compensate for eye distance and pupil size.

A display may tell the person the remaining time for the treatment, which dynamically adjusts for the person's gaze.

Therefore, the person is encouraged to gaze directly at the light source to minimize the session time.

The system may be incorporated into a desk-supported system, portable screens and tablets, smart phones, flat or curved screens, wearable goggles, or other types of flat, curved, round or otherwise differently shaped optical screen or light-source systems.

In another embodiment, the varying LED light may be substantially sinusoidal. This may be done by simply smoothing out the pulses with a low pass filter.

In other embodiments, the power source that pulses the LEDs, or creates a sinusoidal light output, may energize electrodes adhered to the user's skin to provide electric or vibrational stimulation, or may energize a sound system to provide audio stimulation. Any type of sense stimulation will have an effect on the brain to produce or amplify gamma and theta waves in the brain. In one embodiment, light (optical stimulation), skin stimulation, and audio stimulation, or any combination thereof, may occur simultaneously to stimulate various parts of the brain.

The phases of the gamma and theta waves in the brain, as a result of the stimulation, are measured in real-time by, for example, detecting EEG (electroencephalogram) signals, using implants, or using other methods for measurement of brain activity. Then the phase of the light stimulus is controlled (by shifting the stimulus pulses in time) so that the brain is stimulated at a certain phase to ensure optimal neuronal theta-gamma coupling through a phase feedback mechanism. The active measurement of phase during treatment, and then the use of the EEG-feedback to dynamically adjust the stimulus, results in the stimulus being phase-locked to either a natural theta rhythm (the one that is there always) or to an induced theta rhythm (the brain rhythm that is stimulated by light, sound, haptic, electrical/magnetic stimulation. etc.).

BRIEF DESCRIPTION OF THE DRAWINGS

FIG. 5 is a flowchart identifying steps in a broad system process.

Elements labelled with the same numerals in the various drawings may be the same or equivalent.

DETAILED DESCRIPTION

Figure 1:
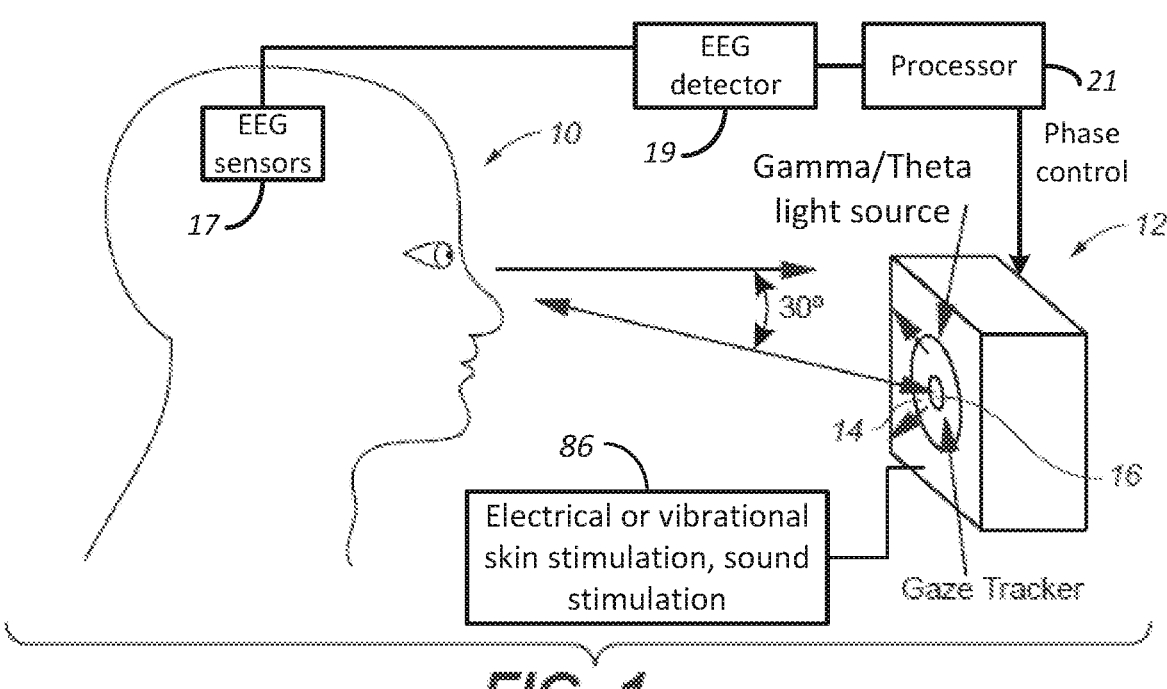
FIG. 1 illustrates the optical gamma/theta brain stimulator with a dosage adjuster, in accordance with one embodiment of the invention.

FIG. 1 illustrates a subject, such as a person 10, that either has been diagnosed with Alzheimer's disease or may be at risk of developing Alzheimer's or other brain disease, or diagnosed with a circadian rhythm sleeping disorder, where the disease or disorder may be treated with optical, modulated gamma/theta brain stimulation. The person 10 may additionally be subjected to or treated with skin or sound gamma/theta brain stimulation.

A gamma/theta brain stimulation light system 12 is positioned about 50-100 cm from the person 10. The system may be supported by a table or desk. In another embodiment, the system forms goggles that are worn by the person 10.

In one embodiment, a pulsing light source 14 uses blue light LEDs, white light LEDs, or a variety of different wavelength monochromatic LEDs.

One set of LEDs is energized at 40 Hz (or other gamma frequency) and another set of LEDs is simultaneously energized at 47 Hz (or other theta frequency). The combined light perceived by the person's brain will be 40 Hz and a beat frequency (subtraction frequency) of 7 Hz. The flickering is near to imperceptible at 40 Hz.

The 40 Hz and 47 Hz frequencies are preferred but not required. A gamma brain stimulation rate range between 20 Hz-140 Hz may be effective, and a theta brain stimulation rate range between 4 Hz-10 Hz may be effective. Therefore, the two light flickering frequencies would differ by 4-10 Hz and be in the range of 20-150 Hz. This would result in the brain being stimulated at the gamma frequency and the beat theta frequency.

The LEDs are optionally arranged to form a circular light source 14 with a camera lens 16 in the middle. In another embodiment, the light source 14 may be more of a point source, and the camera lens 16 may be next to it. In that case, the gaze angle is adjusted for the offset of the lens and the light source. The light source 14 may instead be a flat two-dimensional array of LEDs, such as 20 cm×20 cm diffused Lambertian source.

In another embodiment, the LEDs are energized to output light whose amplitude is sinusoidal. In such a case, the energizing currents to different sets of LEDs are 40 Hz and 47 Hz, so there is no perceived flicker.

In another embodiment, the LEDs are energized for a time (a few seconds) at 40 Hz, followed by being energized for a few seconds at 47 Hz, where the alternation is less than 6 seconds. The brain will perceive the frequencies as being modulated.

In another embodiment, instead of the light alternating between white and darkness, the light can alternate between different colors at the stimulation frequencies, such as between green and red and between blue and yellow. For example, one light source can alternate at 47 Hz between the colors XX and the color YY, and the other light source can alternate at 40 Hz between the colors ZZ and KK. This is referred to as heterochromatic flicker. The heterochromatic flicker can be constructed by multiple combinations of waveforms. Such heterochromatic flicker reduces any noticeable flicker yet produces good results. If the colors are of equal luminance (but still different hues), the flicker should be imperceptible.

The overall dosage of light for the person 10 may be determined by a medical worker based on clinical trials and testing. Optimal dosage levels for different types of persons, such as patients, are still being studied, but a reasonable dosage is one-hour of the person 10 looking directly at the light source 14. Such a session may be performed at the same time every day. The person 10 may be periodically evaluated by a medical worker to correlate the gamma brain stimulation with the effects of Alzheimer's or other disorder. Cognitive testing may be done as well as testing to determine the presence of certain proteins and other chemicals in the person's body. Testing may include an EEG (electroencephalography). It is vital, for evaluation, to know exactly what dosage of light has been given to the person 10.

The Applicants have discovered that the effective dosage of neural entrainment light is highly influenced by combinations of gaze angle, eye distance from the light source, and pupil size, although compensation for any one of these factors helps achieve the target dosage. The actual dosage corresponds to a certain brain stimulation session duration given the particular gaze angles, eye distances, and pupil sizes during the session. Adjustments for gaze angle are the most significant for achieving the target light dosage.

The camera 18 (FIG. 2) and lens 16 may be of a conventional type used for gaze tracking. Conventional software and processing hardware may also be used to detect the gaze angle, eye/face distance, and pupil size. The camera 18 may emit infrared signals and detect the reflection in order to determine the gaze angle, eye/face distance, and pupil size. Alternatively, the camera 18 may use image processing to calculate gaze angle, eye/face distance, and pupil size. Calibration by the person may be initially used to establish baselines, where the person 10 is instructed to look at different areas at different distances to establish the baseline data. That baseline data is then stored in a memory for later comparison to the data collected during a session.

A target light dosage is first established by the medical worker for the person 10 and this information is downloaded into the system 12, such as through the Internet. The target light dosage correlates to the session duration, given a known light optical output power and pulse frequency, with the person at a particular distance from the light source with an average pupil size. In one example, this target dosage assumes the person 10 is directly looking at the light source 14 at a distance of 50 cm with an average pupil size. The actual effective dosage, however, is reduced if the person 10 does not look directly at the light source 14, or is further than 50 cm away, or has a smaller than average pupil size.

As described with respect to FIGS. 2-5, the gaze angle, eye distance from the light source, and pupil size are automatically detected by the camera and algorithms, and the session duration is expanded as necessary to achieve the predetermined target light dosage. For example, a gaze angle of 0° is looking directly at the light source 14, so the person 10 receives 100% of the dosage at 50 cm with average pupil size. A gaze angle of 90° results in the person 10 receiving 0% of the light, and a gaze angle of 45° results in the person 10 receiving 50% of the light. The correlation between detected gaze angle and light reception may be linearly extrapolated between 0-100%, or the correlation may be non-linear based on empirical results.

The detected distance from the light source will have a non-linear correlation to the actual effective dosage, since the effect of the light is non-linearly diminished as the person 10 moves from 50 cm to 100 cm from the light source. Similarly, the pupil size has a non-linear effect on the actual dosage.

Also, as shown in FIG. 1, an EEG feedback system is used to dynamically optimize the phase of the stimulation pulses to maximize coupling between the brain's gamma rhythms and theta rhythms. Recent evidence suggests that good memory performance requires coupling, within the brain, gamma rhythms (about 30-140 Hz) to particular phases of the theta cycle. The theta-gamma coupling is thought to facilitate transfer of information throughout the entorhinal-hippocampal network. Activating gamma-modulated cell assemblies at a particular theta phase may allow the network to produce a more powerful output by ensuring that distributed cells fire closely in time. Such a mechanism may serve to facilitate either memory encoding or memory retrieval, depending on which type of gamma rhythms are recruited.

An EEG is normally used as a test that detects abnormalities in brain waves or abnormalities in the electrical activity of the brain. During the procedure, electrodes consisting of small metal discs with thin wires are pasted onto the user's scalp or positioned close to the scalp such as by using a headpiece. The electrodes detect weak electrical emissions that result from the activity of the brain cells.

We instead detect the EEG signals from the brain to detect the coupling of the gamma and theta rhythms and then adjust the phase of the light stimulation pulses to maximize the coupling.

Figure 6:
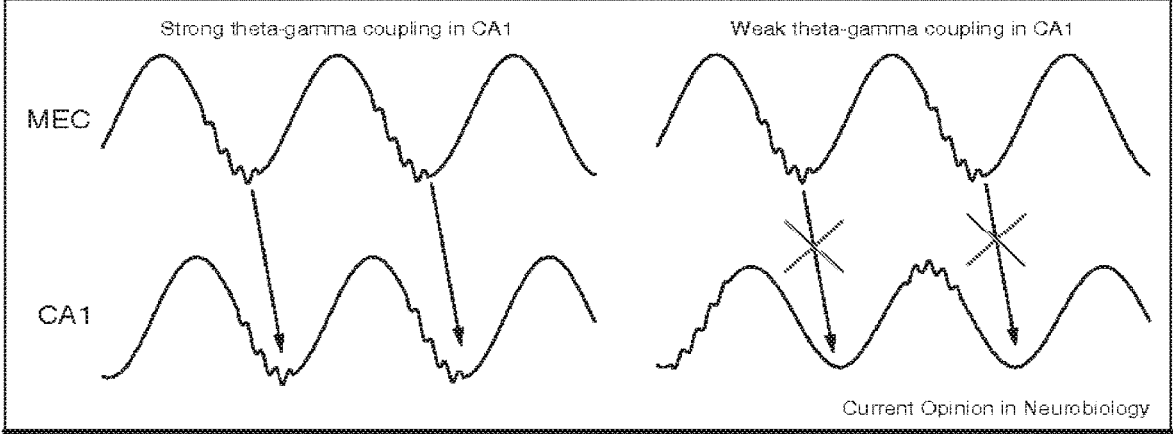
FIG. 6 illustrates the desired theta-gamma wave coupling in the brain.

In FIG. 1, conventional sensors 17, such as metal electrodes, are placed on or near the person's scalp. The EEG signals are sensed using a conventional EEG detector 19. The sensors 17 are placed to sense signals from the medial entorhinal cortex (MEC) and the CAI region of the hippocampus. The correct placement of such sensors 17 would be known to those skilled in the art. The conventional EEG detector 19 then reads the two brain waves. A processor 21 then detects the two waves and adjusts the phase of the light stimulation pulses so the two detected waves have the maximum coupling. This is shown in FIG. 6 where the detected MEC and CAI waveforms on the left show a desirably strong theta-gamma coupling, due to the proper phase adjustment by the processor 21, and the waveforms on the right show a weak theta-gamma coupling, such as prior to the phase adjustment. FIG. 6 is copied from the article semanticscholar.org/paper/Theta % E2%80%93gamma-coupling-in-the-entorhinal % E2%80%93hippocampal-Colgin/4d21566e350ff22f4c03628f5dcaf50fa91430b0. Also with EEG, one can also measure the "surrogate/indirect" effect of phase coupling just from the sensor electrodes. In EEG, we can differ between "source space" and "sensor space". In source space, with enough electrodes, we can measure the phase in the hippocampal and near-hippocampal regions (source space), and in sensor space, using for example frontal or occipital electrodes, we can measure the indirect effects of deep brain phase locking. So, preferably, hippocampus measurements within the source space are used to detect the theta-gamma coupling, but, instead, the coupling can be detected by using the sensor space.

Figure 2:
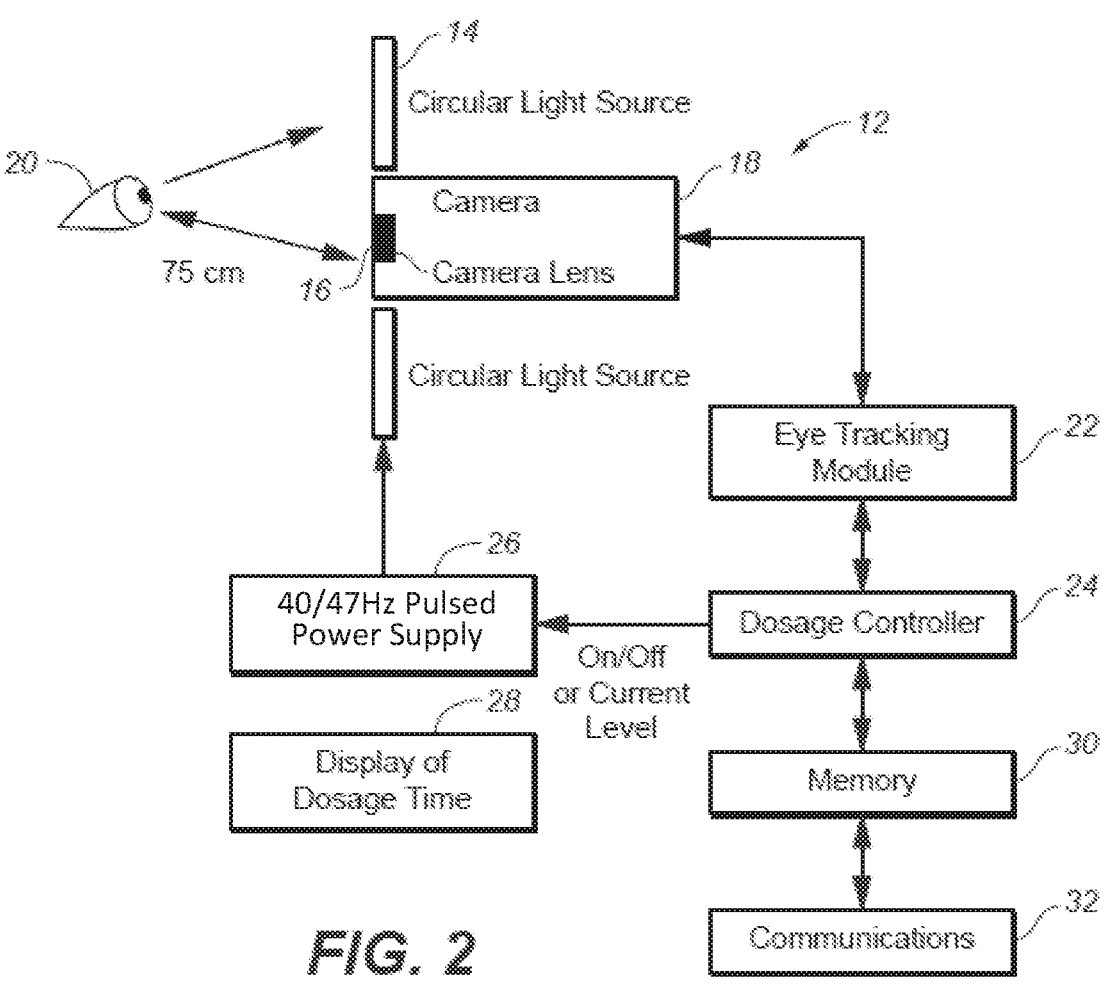
FIG. 2 illustrates various modules in the system.
Figure 3:
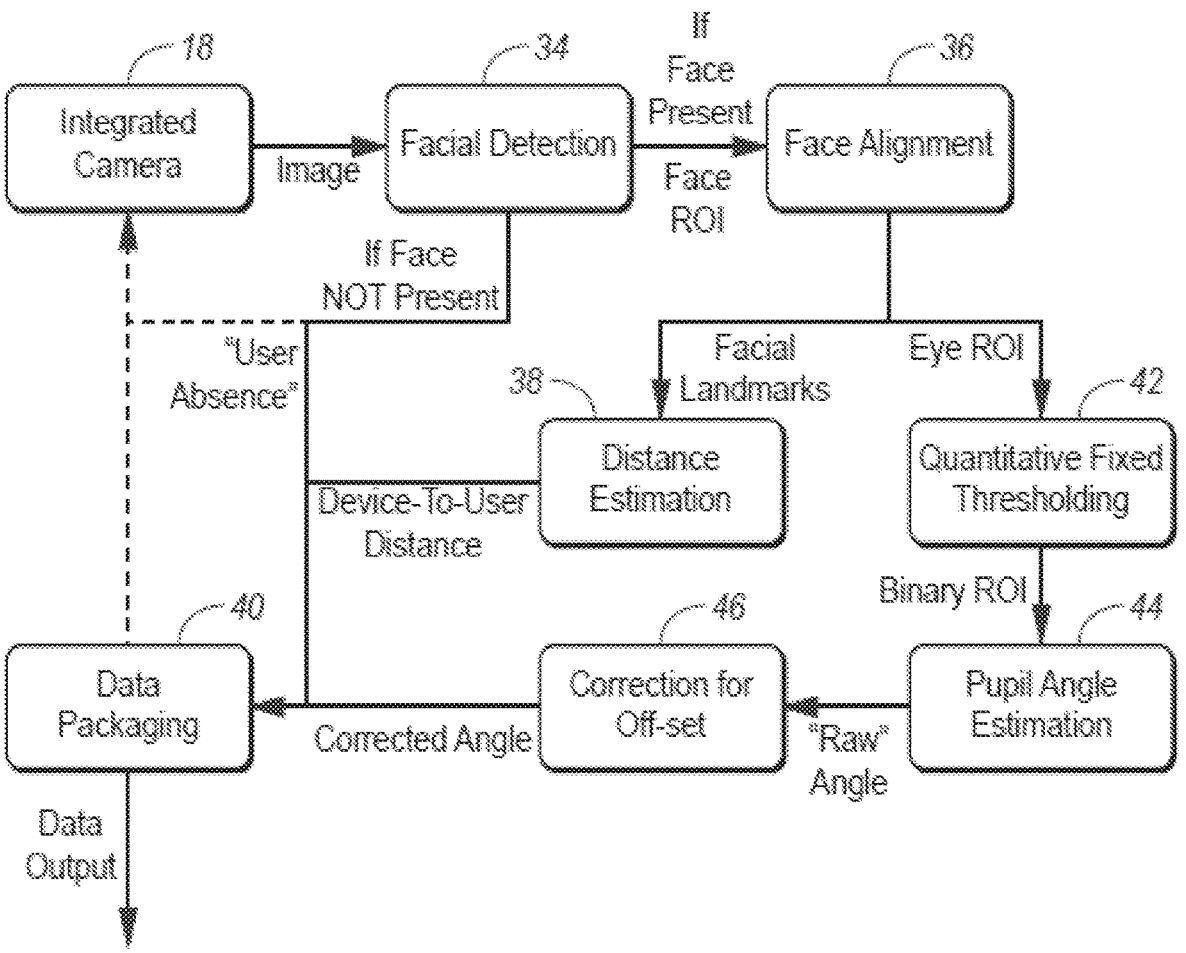
FIG. 3 illustrates the optical detection aspect of the system in more detail.
Figure 4:
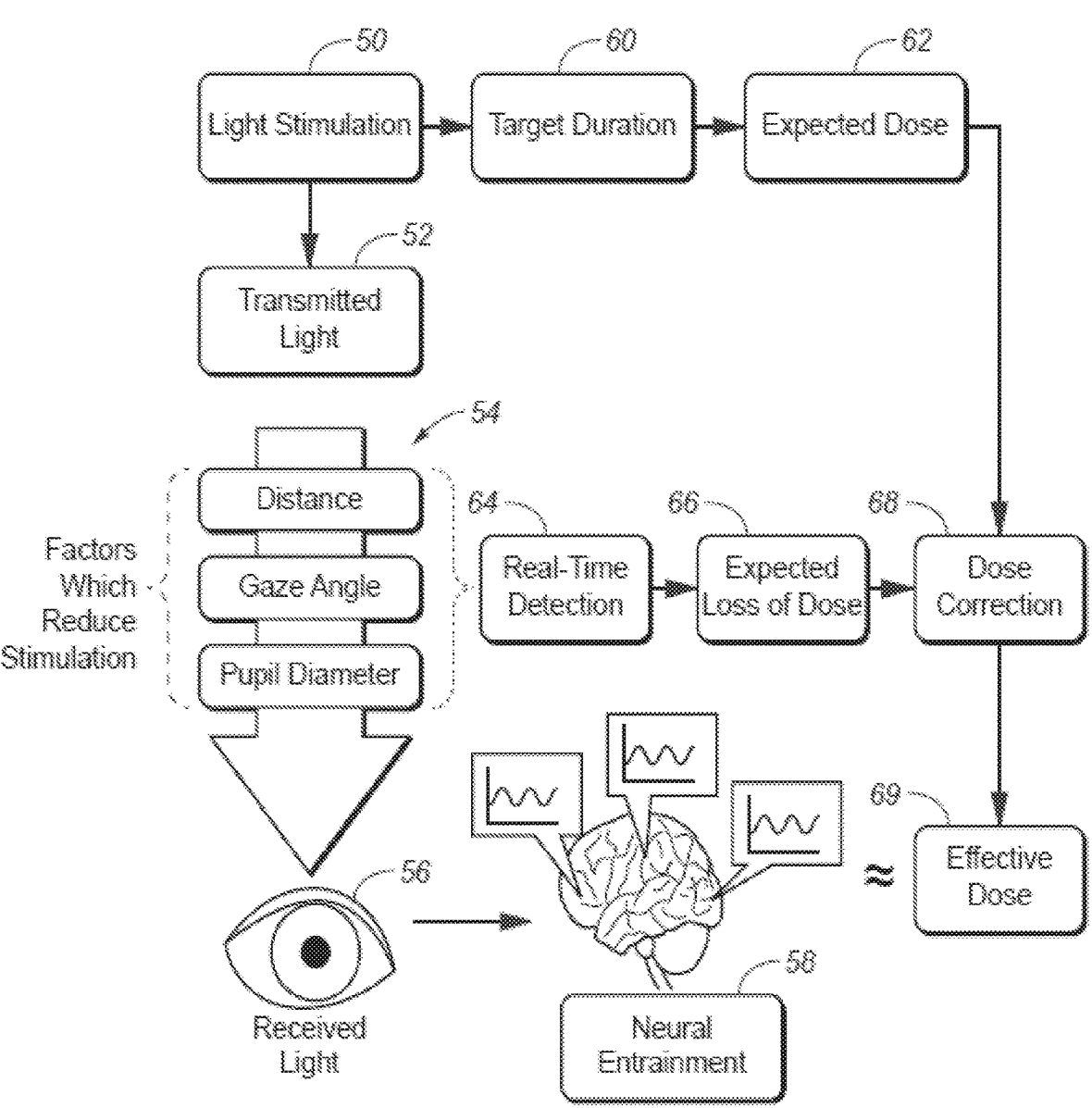
FIG. 4 is a flow chart illustrating the effect of various factors on gamma/theta brain stimulation dosage.

FIGS. 2-4 relate to achieving a predetermined dosage of the light stimulation.

In FIG. 2, the person's eye 20 is assumed to be looking above the light source 14. The camera 18, using image frames or reflected IR light, determines the gaze angle, distance, and pupil size. Gaze detection is commonly used in conjunction with display screens to detect which icon on the screen is being viewed by the viewer, and then to select that icon automatically. Gaze detection is also used in the retail industry to determine where a potential customer is looking. Gaze angle detection, including distance detection, is also used in various other fields and such systems are commercially available and inexpensive.

Suitable gaze detection systems for customization are available from SR Research, Tobii AB, and other companies. A fully customized system can also be fabricated using a Raspberry Pi Camera Module v2 in conjunction with a Raspberry Pi 3 Model B+ single board computer. Much of the software is commercially available.

The raw digital data from the camera 18 is then processed by a processor running an algorithm in the eye tracking module 22. Such algorithms may consist of publically available software customized for the present invention. For the present invention, the software uses the resulting information about gaze angle, distance, and pupil size to dynamically control the dosage so that the person 10 ultimately receives the target dosage, in particular when the person is a patient.

The output of the eye tracking module 22 is then used to adjust the dosage that is controlled by the dosage controller 24. The dosage controller 24 initially receives a target dosage from the medical worker, which may correlate to a one hour session. This target session time is then automatically extended based on deviations from the ideal conditions of direct gaze, 50 cm distance, and average pupil size.

FIG. 2 shows the dosage controller 24 controlling a 40 Hz current pulse power supply and a 47 Hz current power supply 26 to be on a certain amount of time. The dosage controller 24 may also control the current applied to the light source 14. This will result in the person's brain perceiving a 40 Hz pulsed light and a 7 Hz pulsed light due to the beat frequency (subtraction frequency). In one embodiment, both a 40 Hz power supply and a 47 Hz power supply their current to different sets of LED distributed within the light source 14.

In another embodiment, the current supplied to the light source 14 is sinusoidal, and the energizing current is a gamma frequency and the gamma frequency plus a theta frequency.

The required session time is displayed to the person 10 on a display screen 28, so the person 10 knows that the session time has been extended due to the person 10 gazing away or being further than 50 cm from the light source 14. The display screen 28 may use data generated by the local system or generated by a remote system communicating via the Internet.

A memory 30 stores the results of the session so the medical worker has accurate data regarding the dosage.

Communications hardware 32 may convey the data to the medical worker and update the system with upcoming session information.

FIG. 3 illustrates more detail about one embodiment of a suitable camera and algorithms. The algorithms and processor would be within the eye tracking module 22 of FIG. 2. The camera 18 captures an image of the person's face and eye position and analyzes the image. In other systems, IR is reflected off the person and the reflected light is processed. It is assumed that the system has undergone an initial calibration by the person.

In FIG. 3, the face is detected (block 34), such as using a Viola-Jones object detection algorithm. The face is the region of interest (ROI). If a face is detected, the ROI information is passed to a facial alignment block 36 that detects relative distances between facial features for distance estimation (block 38). The calculated distance is then provided in a data package (block 40).

The eyes are also detected and processed by quantitative fixed thresholding algorithms (block 42). This process uses contrast thresholds (binarization) to determine objects, such as irises and pupils. Based on this data, the pupil angle is estimated (block 44). From this, the angle of gaze is computed trigonometrically and, after correcting for any off-set (block 46) of the integrated camera 18 lens relative to the light source, the resulting angle is passed to the data packaging block 40 before capturing the next frame. The dosage may be adjusted dynamically from frame to frame or may just be adjusted nearer the end of the session.

If no face is detected, a "user absence" signal is generated, and no power is applied to the light source.

The packaged data is applied to the dosage controller 24 of FIG. 2, as previously described, to adjust the session duration.

FIG. 4 is a flowchart showing the steps for dynamically controlling the dosage.

In step 50, the 40 Hz/47 Hz strobing light source is turned on to emit the stimulating light 52. The gaze detection system detects the person's distance, gaze angle, and pupil diameter (step 54) as the person's eye receives the light (step 56). The brain then undergoes neural entrainment (step 58) (i.e., the capacity of the brain to naturally synchronize its brainwave frequencies with the rhythm of periodic external stimuli).

The target duration (step 60), provided by the medical worker or other source, is correlated with an expected or target dosage of the light (step 62). The real-time detection (step 64) during the analysis of step 54 is then correlated to any expected loss of dosage (step 66) due to gaze angle, etc. A look-up table may be used to correlate the data with the loss of dosage.

The dose correction step 68 then subtracts the loss of dose from the "ideal conditions" dose to derive the actual effective dose being received by the person. The effective dose information (step 69) is then used to extend the session, as needed, to achieve the target dose.

The data obtained from the session and from testing the person, such as in particular a patient, may be used to further the understanding of the effects of the gamma brain stimulation on, for example, Alzheimer's disease or other neurological or psychiatric disorder (i.e. brain network dysfunctions).

FIG. 5 is a broader flowchart summarizing certain steps in one method to achieve a desired dosage and also maximize theta-gamma coupling in the brain. In step 70, a medical worker or other source communicates to the system the optimal dosage of the gamma/theta brain stimulation, which may be in the form of a session duration time using a known light source.

In step 72, the light source and gaze tracker are activated to start the session.

In step 74, the detected gaze angle, eye distance, and pupil diameter are correlated with a reduction of the effective dosage.

In step 76, the session time is extended, as required, to compensate for the detected gaze angle, eye distance, and pupil diameter. In another embodiment, the target dosage presumes some variation from ideal of the detected gaze angle, eye distance, and pupil diameter, and the system can add or subtract from the session time.

In parallel with detecting the effective dosage, the phase of the light stimulation is controlled to maximize theta-gamma coupling in the brain. The system for adjusting the phase was described with respect to FIG. 1. In step 78, the EEG signals from the MEC and CA1 areas of the brain are detected using sensors.

In step 80, the EEG signals are processed, and the phase of the light stimulation system is dynamically adjusted so that the two detected EEG signals have a high coupling, such as shown on the left side of FIG. 6.

In step 82, the session data is stored in a memory for evaluating the efficacy of the treatment.

In step 84, a communications system conveys the data to a clinic or other medical worker. The communications system can also receive information, such as the target dose.

The system may be used for therapy or just to analyze the effects of the optical gamma/theta brain stimulation on a group of similar persons for collecting further data for study. Other strobing frequencies besides 40 Hz and 47 Hz, as previously mentioned, may prove valuable with further studies.

The invention is not limited to a gamma/theta brain stimulation rate of 20-140 Hz and 4-10 Hz. Other frequency light pulses emitted by the light source 14 may be beneficial for beta brain waves (beta brain stimulation rate of 13-38 Hz) and circadian functions. By generating light greater than a frequency that causes perceptible flicker, and also generating light at that frequency plus a lower frequency, the original frequency and the subtraction frequency are perceived internal to the brain without the detection of flicker.

In another embodiment, the system is only used for gamma wave stimulation.

In other embodiment, the optical system of FIG. 1 is combined with other systems that stimulate other senses, such as feel and hearing. The energizing of the LEDs in the light source 14 may also trigger electrical pulses to electrodes adhered to the person's skin to provide mild shocks, and/or the electrical signals may trigger sound pulses. Thus, different areas of the brain are simultaneously stimulated with the exact same gamma and theta waves. This skin and sound system is represented by the functional block 86 in FIG. 1.

The phases of the gamma and theta waves may also be varied for testing the results of different phases.

DEFINITIONS

The term "gamma/theta brain stimulation" means a stimulus, such as a light source, that can change the neuronal gamma and theta activity in the brain.

The term "person" means a subject to be subjected to gamma/theta brain stimulation, such as a patient exhibiting symptoms of a brain disease such as Alzheimers, or such as a person who desires pre-emptive gamma/theta brain stimulation, or a test-person who is subjected to gamma/theta brain stimulation for instructive or test purposes.

The term "stimulation session" means a procedure over time where the person is exposed to a brain-stimulating device to receive a certain dosage of light. A single stimulation session is typically conducted within a day, but a customized session can be expanded and individualized to comprise multiple days, weeks, or months.

The term "stimulation duration" means a time period of a stimulation session, but is not limited to comprising the whole session duration, since the stimulation session time period can be broken up into multiple individual durations allowing for "interval" training, such as 15 minutes×4=60 minute session.

Strobing and flickering are used interchangeably in this application.

While particular embodiments of the present invention have been shown and described, it will be obvious to those skilled in the art that changes and modifications may be made without departing from this invention in its broader aspects and, therefore, the appended claims are to encompass within their scope all such changes and modifications that are within the true spirit and scope of this invention.

What is claimed is:

1. A brain stimulation system for a person comprising:
one or more power supplies controlled by a processing system to energize a first light source and a second light source;
the first light source coupled to the one or more power supplies being controlled to generate light only at a first brain stimulation rate within a gamma wave range of 20-140 Hz, the second light source coupled to the one or more power supplies being controlled to generate light at a second brain stimulation rate of the first brain stimulation rate plus a theta wave range of 4-10 Hz;
a feedback system configured to detect the person's brain waves and generate first signals that correspond to rhythmic patterns in the brain waves; and
the processing system coupled to detect the first signals corresponding to the rhythmic patterns in the brain waves and coupled to control the one or more power supplies to adjust phases of the generated light from the first light source and the second light source to phase-lock the generated light to the rhythmic patterns in the brain waves to increase theta-gamma wave coupling in the person's brain.

2. The system of claim 1 wherein the one or more power supplies controls the first light source and the second light source simultaneously to simultaneously generate the light at the first brain stimulation rate of a first frequency within the gamma wave range of 20-140 Hz and the light at the second brain stimulation rate of a second frequency that is greater than the first frequency by 4-10 Hz.

3. The system of claim 1 wherein a first power supply of the one or more power supplies controls a first set of light emitting diodes (LEDs) within the first light source at the first brain stimulation rate, and wherein a second power supply of the one or more power supplies controls a second set of LEDs within the second light source at the second brain stimulation rate.

4. The system of claim 1 wherein the feedback system comprises one or more EEG sensors for detecting the brain waves.

5. The system of claim 4 wherein the one or more EEG sensors detects electrical emissions from at least one of the medial entorhinal cortex (MEC) and hippocampus areas of the person's brain.

6. The system of claim 1 further comprising:
an eye-tracking device that detects said person's eye and provides first data to the processing system indicative of an amount of the light from the first light source and the second light source being received by the person's eye,
wherein the processing system is configured to use the first data to adjust a duration of the brain stimulation session.

7. The stimulation system of claim 6 wherein the eye-tracking device determines a person's gaze angle, and the first data corresponds to the person's gaze angle with respect to the first light source and the second light source.

8. The stimulation system of claim 6 wherein the eye-tracking device determines a person's distance from the first light source and the second light source, and the first data corresponds to the person's distance to the first light source and the second light source.

9. The stimulation system of claim 6 wherein the eye-tracking device determines a person's pupil size, and the first data corresponds to the person's pupil size.

10. The stimulation system of claim 6 wherein the processing system is configured to extend the duration of the brain stimulation session based on the first data.

11. The stimulation system of claim 6 further comprising a display of a duration of the brain stimulation session as the session is adjusted.

12. The stimulation system of claim 6 wherein the eye-tracking device comprises a camera.

13. The simulation system of claim 1 wherein the first light source generates light that alternates between at least two different colors, in a first set of colors, to generate heterochromatic flicker at the first brain stimulation rate, and wherein the second light source generates light that alternates between at least two different colors, in a second set of colors, to generate the heterochromatic flicker at the second brain stimulation rate.

14. The system of claim 1 wherein the first light source is strobed at the first brain stimulation rate, and wherein the second light source is strobed at the second brain stimulation rate.

15. A brain stimulation method for a person comprising:

controlling a first light source only at a first brain stimulation rate in a gamma wave range between about 20-140 Hz; and simultaneously controlling a second light source at a second brain stimulation rate of the first brain stimulation rate plus a theta wave range of 4-10 Hz;

detecting the person's brain waves using a feedback system and generating first signals that correspond to rhythmic patterns in the brain waves; and controlling the one or more power supplies to adjust phases of the generated light from the first light source and the second light source to phase-lock the generated light to the rhythmic patterns in the brain waves to increase theta-gamma wave coupling in the person's brain.

16. The method of claim 15 wherein the first light source comprises one or more first light emitting diodes (LEDs) controlled at the first brain stimulation rate, and the second light source comprises one or more second LEDs controlled at the second brain stimulation rate.

17. The method of claim 15 wherein detecting the person's brain waves comprises detecting the brain waves using one or more EEG sensors.

18. The method of claim 15 wherein the first light source generates light that alternates between at least two different colors, in a first set of colors, to generate heterochromatic flicker at the first brain stimulation rate, and wherein the second light source generates light that alternates between at least two different colors, in a second set of colors, to generate the heterochromatic flicker at the second brain stimulation rate.

* * * * *